United States Patent [19]

Hoegnelid et al.

[11] Patent Number: 5,423,871
[45] Date of Patent: Jun. 13, 1995

[54] METHOD AND DEVICE FOR MONITORING ELECTRODES OF ELECTRICAL HEART STIMULATORS

[75] Inventors: Kurt Hoegnelid, Västerhaninge; Hans Strandberg, Sundbyberg, both of Sweden

[73] Assignee: Pacesetter AB, Solna, Sweden

[21] Appl. No.: 178,837

[22] Filed: Jan. 7, 1994

[30] Foreign Application Priority Data

Jan. 29, 1993 [SE] Sweden .................. 93002830

[51] Int. Cl.$^6$ .............................................. A61N 1/37
[52] U.S. Cl. .................................. 607/28; 607/27; 607/62; 128/734
[58] Field of Search .............. 607/2, 6, 15, 27, 28; 128/734

[56] References Cited

U.S. PATENT DOCUMENTS

| | | | |
|---|---|---|---|
| 4,140,131 | 2/1979 | Dutcher et al. | 128/419 |
| 4,719,922 | 1/1988 | Padjen et al. | 128/421 |
| 4,785,812 | 11/1988 | Pihl et al. | 128/419 |
| 4,805,621 | 2/1989 | Heinze et al. | 128/734 |
| 4,899,750 | 2/1990 | Ekwall | 128/734 |
| 5,027,813 | 7/1991 | Pederson et al. | 128/734 |
| 5,179,945 | 1/1993 | Weiss | 128/734 |
| 5,201,865 | 4/1993 | Kuehn | 607/28 |
| 5,215,081 | 6/1993 | Ostroff | 128/734 |

FOREIGN PATENT DOCUMENTS 0360551 3/1990 European Pat. Off. .

Primary Examiner—William E. Kamm
Assistant Examiner—Kennedy J. Schaetzle
Attorney, Agent, or Firm—Hill, Steadman & Simpson

[57] ABSTRACT

In a method for continuous, electrical monitoring of the electrodes of an electrical heart stimulator, having at least one stimulation electrode and an indifferent electrode, the inter-electrode voltage is kept constant by regulation of a very low compensating current, and the magnitude of this current is measured and monitored. A device for such electrode monitoring includes control electronics and an output stage for delivery to the stimulation electrode of stimulation pulses. The output stage is devised to supply the electrodes with a weak, continuous current, or a repeated, pulsed current, producing a net direct current, in addition to stimulation pulses. A monitoring unit senses the inter-electrode voltage and, on the basis thereof, deliver an output signal to the control electronics for the purpose of controlling the weak current so the inter-electrode voltage is kept constant at a given value. This output signal is monitored, with significant deviations thereof, or an inability to maintain the inter-electrode voltage constant indicating the presence of a fault in the electrode system.

11 Claims, 2 Drawing Sheets

METHOD AND DEVICE FOR MONITORING ELECTRODES OF ELECTRICAL HEART STIMULATORS

BACKGROUND OF THE INVENTION

1. Field of the Invention

The present invention relates to a method and device for continuous, electrical monitoring of the electrodes of an electrical heart stimulator, the heart stimulator including at least one stimulation electrode, one indifferent electrode, control electronics and an output stage for delivery of stimulation pulses to the stimulation electrode.

2. Description of the Prior Art

Damage to and other faults in the electrode system of an electrical heart stimulator can develop, making reliable heart stimulation impossible. During checks on implants at clinics and hospitals, the electrode system is also checked non-invasively. The magnitude of electrode impedance, i.e. stimulation impedance, and the appearance of pulses from surface ECG electrodes can supply information about electrode defects in the heart stimulator.

Such known methods, however, are uncertain and subjective and only reliable when "major" defects, such as electrode fracture, are present. The necessity that the check can only be made when the patient visits a clinic or hospital is also unsatisfactory.

A method and a device are described in European Application 0 437 104 for measuring electrode resistance with sub-threshold pulses supplied to defibrillation electrodes before a defibrillation shock is delivered. Only one current pulse with a predetermined magnitude is emitted across the electrodes and the resulting voltage is measured and the resistance calculated.

In U.S. Pat. No. 4,140,131 an implantable heart stimulator is described with two impedance detectors, i.e. a low impedance level detector and a high impedance level detector, which supply a warning if the stimulator's output impedance is outside a predetermined impedance range. The detectors compare the voltage measured across a series resistor in the electrode circuit upon the delivery of stimulation pulses with preset limit values.

Thus, the need for electrode monitoring of implantable heart stimulators is well-known and has hitherto been accomplished in different ways, such as direct measurement on the electrode, with no stimulator connected, or by delivery of stimulation pulses, the impedance of pulses being calculated with some appropriate measurement method. The measurement value is then transmitted by telemetry, and the doctor decides whether the impedance value designates a fault-free electrode system.

SUMMARY OF THE INVENTION

An object of the present invention is to provide a new method and to provide a new device for continuous electrical electrode monitoring of implantable electrical heart stimulators with the aid of a continuous current or a repeated, pulsed current. This provides a net direct current, which is so weak that it is negligible compared to the currents for e.g., pacemaker stimulation.

The above object is achieved in a method and apparatus in accordance with the principles of the present invention wherein the voltage between the stimulation electrode and the indifferent electrode is maintained constant by regulating a weak compensating current, and the magnitude of the compensating current is measured and monitored.

Thus, in the method and device a known variable, controlled current is delivered in order to maintain a given, constant electrode voltage. Any fault in the electrode system manifests itself as currents of highly varying magnitudes or as an inability to maintain a constant electrode voltage. An appropriate electrode voltage is of the order of magnitude of 0.5 V and an appropriate current is of the order of magnitude of 50 nA. In the method and device of the invention, it is not meaningful to speak of an electrode impedance, since tile impedance would, with the new measurement technique according to the invention, amount to 10 Mohm in a fault-free electrode system. It should be noted that the so-called "pulse impedance" is not the parameter measured in the method and device according to the invention. The pulse impedance normally amounts to about 500 ohms.

The galvanic system formed by the electrodes and body fluid is affected both by interruptions and short-circuits in the electrode system, and these faults will appear in the electrical quantities.

In a further embodiment of the method according to the invention, the current to the electrodes is feedback-regulated so a constant voltage is maintained, a feedback current being measured and monitored as the compensating current. This makes possible a simple realization of the invention.

Thus, continuous electrode monitoring with a very low consumption of current is achieved with the present invention.

DESCRIPTION OF THE PREFERRED EMBODIMENTS

Figure 1:
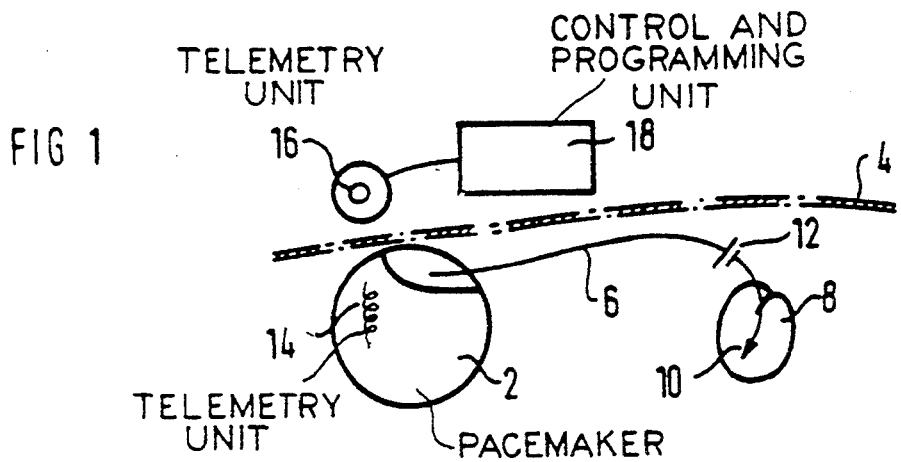
FIG. 1 schematically depicts an implanted pacemaker with telemetry equipment and a monitoring device according to the invention.

An implanted pacemaker is schematically shown in FIG. 1 beneath the patient's skin 4. The pacemaker 2 is, via an electrode cable 6, connected to a stimulation electrode 10 implanted in the heart 8. Damage to the electrode cable 6 is marked at 12, this damage being detectable with the present invention. The pacemaker 2 is equipped with a device (not shown in this FIG. 1) according to the invention for monitoring the electrode. The pacemaker 2 is further provided with a telemetry unit, indicated at 14, for communications with an external telemetry unit 16 connected to an external control and programming unit 18. Information about e.g., the condition of the electrode can be retrieved via this control and programming unit 18.

Figure 2:
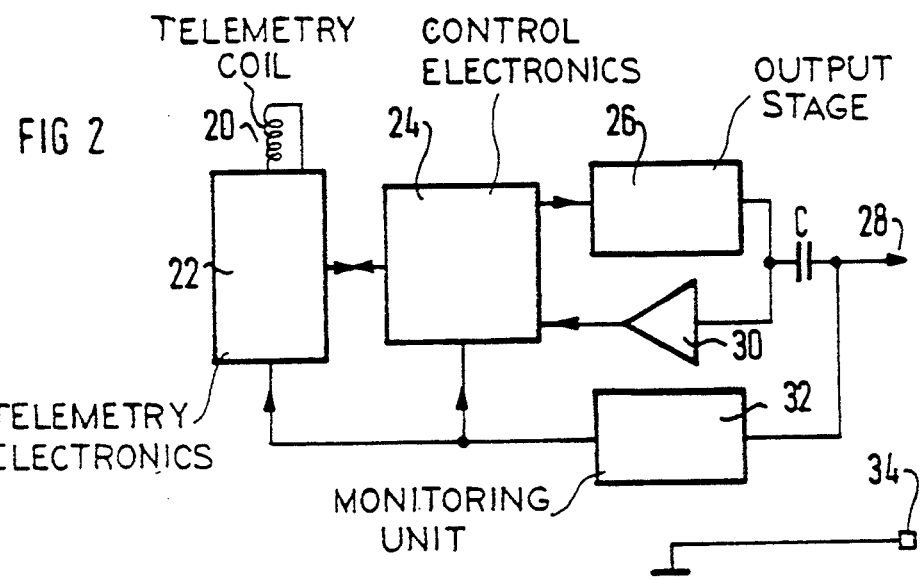
FIG. 2 is a block diagram of a pacemaker equipped with a monitoring device according to the invention.

FIG. 2 shows a block diagram of a pacemaker which contains, in the conventional way, a telemetry coil 20 with associated telemetry electronics 22 connected to the pacemaker's control electronics 24. The control electronics 24 control an output stage 26 for supplying stimulation pulses to the stimulation electrode 28 via an output capacitor C. A heart signal detector 30 is also connected to the electrode 28, which delivers sensed heart signals to the control electronics 24 so stimulation takes place in response to detected heart signals.

The pacemaker in FIG. 2 is further equipped with a monitoring unit 32 which senses the voltage of the stimulation electrode 28 in relation to the indifferent electrode 34. The monitoring unit 32 delivers an output signal to the control electronics 24 according to the voltage measured between the electrodes 28 and 34, so a current can be supplied to the electrodes to keep the voltage between them constant at a defined value between stimulation pulses. A suitable inter-electrode voltage can typically amount to about 0.5 V, and the emitted current can typically amount to about 50 nA.

The damage to the electrode system could be manifested as severe deviation in the magnitude of the current or as an inability to maintain the inter-electrode voltage at a constant value. The output terminal of monitoring unit 32 is also connected to the telemetry electronics 22, making external electrode monitoring possible.

The current employed for the electrode monitoring is so weak that it is negligible compared to the stimulation current. Thus, electrode monitoring according to the invention causes a negligible increase in total current consumption. The current used for electrode monitoring in order to maintain the voltage between the electrodes can either be a continuous current or a repeated, pulsed current, supplying a net direct current, as noted above.

Figure 3:
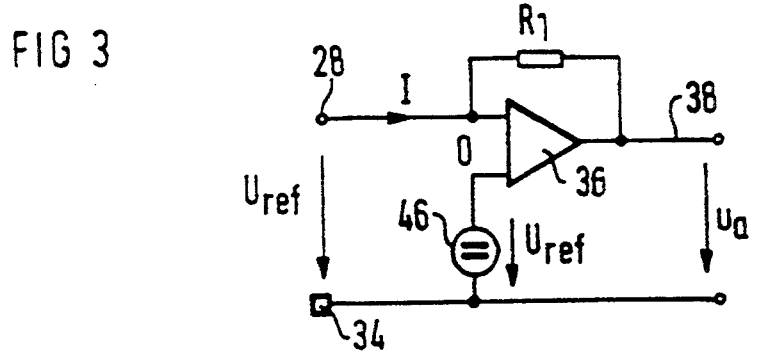
FIGS. 3 and 4 respectively show two alternative versions of the comparator circuit in the device according to the invention.

FIG. 3 shows a comparator 36 in the monitoring unit 32 for comparing the voltage between the electrodes 28 and 34 with a predetermined reference value $U_{ref}$. The comparator 36 has low-resistance output so it can be heavily loaded, and consists of an amplifier which is feedback-coupled through a resistor $R_1$. The resistance of the comparator's input is so high that the input current is negligible compared to the measurement current. An output signal is obtained at the output 38 of the comparator 36 representing the "fault voltage" which, possibly via an A/D converter, is supplied to the control electronics 24 to adjust the monitoring voltage against the desired value.

The following relationship exists between the voltage $U_a$ at the output 38, the current I and the voltage $U_{ref}$:

$$U_a = -I \cdot R_1 + U_{ref}$$

For $R_1 = 2$ Mohms and $I = 1$ nA, the fault voltage $U_{ref} - U_2 = 2$ mV is obtained.

Figure 4:
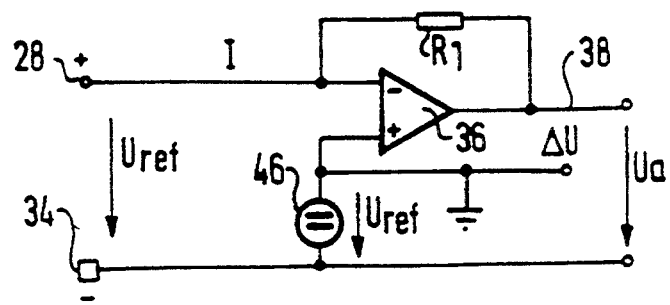

A modification of the circuit of FIG. 3 is shown in FIG. 4 in which the connection point between the amplifier forming the comparator 36 and the source of reference voltage 46 is grounded. The fault voltage then becomes $$\Delta U = U_{ref} - U_a = I \cdot R_1$$

In this case, a fault voltage to ground U, which is directly proportional to the current I, is obtained at the output 38 of the amplifier. Thus, the feedback current constitutes the measurement parameter. A fault voltage is measured and a current is supplied to correct the fault voltage.

Figure 5:
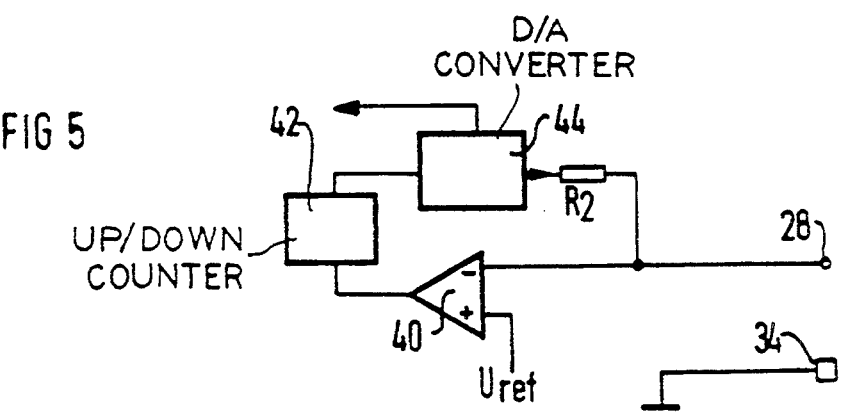
FIG. 5 shows a version for control and monitoring of the device according to the invention.

FIG. 5 shows an alternative version in which the amplifier 40 is feedback-coupled via an up/down counter 42, a D/A converter 44 and a resistor $R_2$. The up/down counter 42 increments during the time the measured voltage is less than the reference voltage $U_{ref}$ and decrements during the time the measured Voltage exceeds the reference voltage $U_{ref}$ in order to induce the D/A converter 44 to deliver an analog signal representing the "fault voltage". The output signal from the D/A converter 44 is utilized for monitoring purposes and for regulating the voltage, required for electrode monitoring, between the electrodes 28 and 34 toward the predetermined, constant value.

Figure 6:
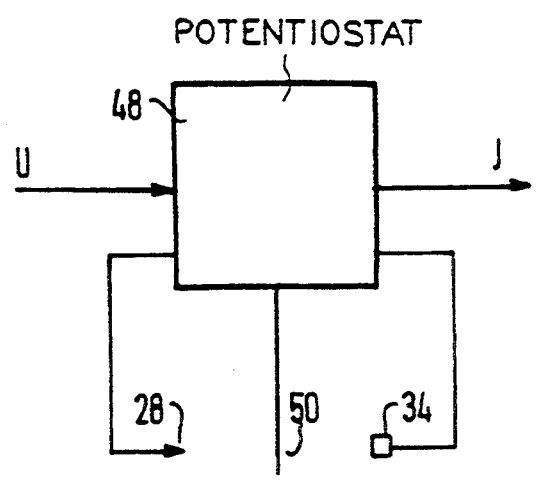
FIG. 6 shows an embodiment of the device according to the invention with the monitoring unit containing a potentiostat.

FIG. 6 shows an embodiment in which the monitoring unit includes a potentiostat 48 which keeps the stimulation electrode 28 at a constant potential in relation to a third reference electrode 50, the current between the stimulation electrode 28 and the indifferent electrode 34 then being monitored.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for continuously electrically monitoring a stimulation electrode and an indifferent electrode in an electrical cardiac stimulator, comprising the steps of:
    maintaining a voltage between said electrodes constant by regulating a weak compensating current; and
    monitoring the magnitude of said compensating current as indicative of the presence of damage to one of said electrodes.

2. A method as claimed in claim 1 wherein the step of maintaining said voltage between said electrodes constant is further defined by supplying a weak, continuous current to said electrodes;
    regulating said weak continuous current by feedback to maintain said voltage at a constant, and thereby obtaining a feedback current; and
    monitoring said feedback current as said compensating current.

3. A method as claimed in claim 1 wherein the step of maintaining said voltage between said electrodes at a constant is further defined by supplying a weak, pulsed current providing a net direct current to said electrodes;
    regulating said weak, pulsed current by feedback to maintain said voltage between said electrodes at a constant, and thereby obtaining a feedback current; and
    monitoring said feedback current as said compensating current.

4. In an electrical cardiac stimulator having at least one stimulation electrode, an indifferent electrode, and output means for delivering electrical stimulation pulses via said electrodes, the improvement of a device for continuously electrically monitoring said electrodes, said device comprising:
    control means for controlling said output stage to supply said electrodes with a weak current in addition to said stimulation pulses;
    monitoring means for sensing a voltage between said electrodes and for supplying an output signal to said control means for controlling said weak current for maintaining said voltage constant at a defined value; and means for monitoring said output signal to determine if said voltage deviates from said defined value.

5. A device as claimed in claim 4 wherein said monitoring means comprises comparator means formed by a feedback amplifier for comparing said voltage between said electrodes with a predetermined reference value.

6. A device as claimed in claim 4 wherein said monitoring means comprises:
   up/down counter means for incrementing if said voltage between said electrodes is less than a selected reference value and for decrementing if said voltage between said electrodes exceeds said reference value; and
   a digital-to-analog converter for converting an output from up/down counter means into an analog signal, said analog signal forming said output signal.

7. A device as claimed in claim 4 wherein said monitoring means comprises:
   a feedback amplifier having a first input connected to one of said electrodes, and having a second input;
   a voltage source which generates a predetermined voltage value connected between said second input of said feedback amplifier and the other of said electrodes, said feedback amplifier generating a fault voltage proportional to a current between said electrodes, said fault voltage comprising said output signal.

8. A device as claimed in claim 7 further comprising a connection to ground between said feedback amplifier and said voltage source, said feedback amplifier generating a fault voltage relative to ground which is directly proportional to said current between said electrodes, said fault voltage relative to ground comprising said output signal.

9. A device as claimed in claim 7 wherein said stimulation electrode is adapted to be connected to said first input of said feedback amplifier and wherein said indifferent electrode is adapted to be connected to said voltage source.

10. A device as claimed in claim 4 further comprising a third electrode, and wherein said monitoring means comprises a potentiostat which maintains said stimulation electrode at a constant potential in relation to said third electrode, and wherein said means for monitoring said output signal comprise means for monitoring a current between said stimulation electrode and said indifferent electrode.

11. A device as claimed in claim 4 further comprising means for telemetrically supplying said output signal from said cardiac stimulator to an external device.

* * * * *